(12) United States Patent
Gonzalez

(10) Patent No.: US 8,361,042 B1
(45) Date of Patent: Jan. 29, 2013

(54) FAT HARVESTING CONTAINER

(76) Inventor: Ruben Gonzalez, Miami, FL (US)

(*) Notice: Subject to any disclaimer, the term of this patent is extended or adjusted under 35 U.S.C. 154(b) by 590 days.

(21) Appl. No.: 12/684,679

(22) Filed: Jan. 8, 2010

Related U.S. Application Data

(63) Continuation-in-part of application No. 12/419,575, filed on Apr. 7, 2009, now Pat. No. 8,172,832.

(51) Int. Cl.
*A61M 1/00* (2006.01)

(52) U.S. Cl. ......... 604/317; 604/324; 604/326; 604/542

(58) Field of Classification Search .......... 604/317–319, 604/322, 324, 326, 542
See application file for complete search history.

(56) References Cited

U.S. PATENT DOCUMENTS

| | | | | |
|---|---|---|---|---|
| 3,866,608 A | * | 2/1975 | Reynolds et al. | 604/319 |
| 4,306,557 A | * | 12/1981 | North | 604/119 |
| 8,100,874 B1 | * | 1/2012 | Jordan et al. | 604/319 |
| 2009/0287190 A1 | * | 11/2009 | Shippert | 604/542 |

* cited by examiner

*Primary Examiner* — Lynne Anderson
(74) *Attorney, Agent, or Firm* — Albert Bordas, P.A.

(57) ABSTRACT

A fat harvesting container, having a transparent container assembly with a top edge, a base, an exterior wall with first and second sections, and an incline wall. The first section extends from the top edge to the base. The second section extends from the top edge to the inclined wall, and the inclined wall extends from the second section to the base. The transparent container assembly also comprises a first outlet. The fat harvesting container also comprises a lid assembly, a tubing assembly, and a first valve assembly. The inclined wall biases liquid matter towards the first outlet, thus facilitating its exit therethrough with minimum movement of liquid matter and fat matter within the transparent container assembly. This way liquid matter and fat matter remain separate and a probability of remixing is reduced and prevented.

15 Claims, 4 Drawing Sheets

FAT HARVESTING CONTAINER

II. BACKGROUND OF THE INVENTION

1. Field of the Invention

The present invention relates to medical collecting containers, and more particularly, to fat harvesting containers.

2. Other Related Applications.

The present application is a continuation-in-part of pending U.S. patent application Ser. No. 12/419,575, filed on Apr. 7, 2009, which is hereby incorporated by reference.

3. Description of the Related Art.

Liposuction, also known as lipoplasty, liposculpture suction lipectomy, or simply lipo (suction-assisted fat removal) is a cosmetic procedure that removes fat from many different sites of the human body. Since liposuction procedures have become more widely available, fat has also become more easily withdrawn from the body. That development has allowed more plastic, dermatological, and cosmetic surgeons to offer their patients fat transfer for cosmetic reasons. Patients like fat transfer because it is their own tissue and, hence, not subject to rejection by the body. However, the safety of the technique relates not only to the amount of tissue removed, but also to the harvesting of fat to be transferred.

Essentially, the fat transfer procedure harvests fat from one part of the body, where an excess exists, and then places it in another part of the body where the additional bulk is used for cosmetic and aesthetic purposes. Fat transfer, which is also known as fat grafting, autologous fat transplantation, fat injecting, or microlipoinjections, may be used to smooth and repair aged hands; fill wrinkled and creased faces; create more shapely, curvaceous buttocks; or enlarge breasts as an example.

In the most common used procedures, fat is withdrawn from the patient with a syringe that has a large bore needle or with a liposuction cannula. The fat is prepared according to the practitioner's preferred method and then injected into the patient's recipient site. The preparation process needs to clear the donor fat of blood and other unwanted ingredients that could cause undesirable side effects. Moreover, some physicians have found that human fat outside the body is incredibly delicate. An important fact of the survival of injected fat seems to depend on how the physician harvests the donor fat, the technique used to treat the fat, and how the prepared fat cells are put back into the patient. Therefore, the procedure is operator dependent and relies on the techniques of harvesting, cleansing, and reinjection.

In order to prepare the fat tissue for injection, it must be separated from other harvested substances in a mixture, whereby the mixture is manipulated in a variety of ways in order to remove oil, blood, and tumescent fluid layers for the transfer of the fat tissue. The transfer of the fat tissue is usually made to smaller transplantation syringes for transplantation. Various manipulation techniques involve rotating and moving the mixture from one container to another. Often, the fat tissue is injected into another container to be washed, and then injected into the smaller transplantation syringes so that it may then be injected into the desired location. Each of these manipulations exposes at least some of the mixture and the fat tissue therein to air. In addition, they bring the mixture and tissue into contact with additional instruments and surfaces, often causing trauma to the tissue. Each exposure to air reduces the viability of the fat tissue, and increases the risk of contamination. Each manipulation of the mixture, and the fat tissue contained therein, affects the results of the transplantation. The compromised sterility increases the chances of infection, inflammation, and rejection of the fat transplant.

Other methods and apparatus related to the subject matter provide for a number of more or less complicated features that fail to solve the problem in an efficient and economical way. None of these methods and apparatus suggest the novel features of the present invention.

III. SUMMARY OF THE INVENTION

The instant invention is a medical collecting container for harvesting human body fat. More specifically, the instant invention is a fat harvesting container, comprising a transparent container assembly having a top edge, a base, an exterior wall with first and second sections, and an incline wall. The first section extends from the top edge to the base. The second section extends from the top edge to the inclined wall, and the inclined wall extends from the second section to the base. The transparent container assembly also comprises a first outlet. The instant invention also comprises a lid assembly, a tubing assembly, and a first valve assembly.

The lid assembly comprises a top wall having a second outlet and a first inlet. The lid assembly also comprises a sidewall and a channel that aligns with to receive the top edge when the lid assembly is placed thereon with a predetermined force to seal the transparent container assembly. The first valve assembly comprises a second inlet, a third outlet, and a fourth outlet. The first valve assembly is removably mounted onto the first outlet. The tubing assembly comprises at least first, second, third, and fourth tubes, and a second valve assembly. The first tube is connected to a vacuum pump and to the second valve. The second tube is connected to the second valve assembly and the second outlet. The third tube is connected to the first inlet and tooling to obtain emulsion from a patient. The fourth tube is connected from the third output of the first valve assembly to the second valve assembly.

It is therefore one of the main objects of the present invention to provide a medical collecting container that safely harvests human body fat.

It is another object of the present invention to provide a medical collecting container for harvesting human body fat that minimizes exposure to air and bacteria.

It is another object of the present invention to provide a medical collecting container for harvesting human body fat that increases fat tissue viability.

It is another object of the present invention to provide a medical collecting container for harvesting human body fat that reduces contamination risks.

It is yet another object of the present invention to provide a medical collecting container for harvesting human body fat that minimizes manipulation of a mixture and fat tissue contained therein.

It is yet another object of the present invention to provide a medical collecting container for harvesting human body fat that, maximizes sterility of the mixture and tissue.

It is yet another object of the present invention to provide a medical collecting container for harvesting human body fat, comprising a one-piece integral container assembly.

It is yet another object of the present invention to provide a medical collecting container for harvesting human body fat, having conveniently shaped bottom and outlet to facilitate the exit while minimizing commingling of matter contained therein.

It is still another object of the present invention to provide a medical collecting container for harvesting human body fat that is volumetrically efficient for carrying, transporting, and storage.

It is still another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

IV. BRIEF DESCRIPTION OF THE DRAWINGS

With the above and other related objects in view, the invention consists in the details of construction and combination of parts as will be more fully understood from the following description, when read in conjunction with the accompanying drawings in which.

V. DETAILED DESCRIPTION OF THE PREFERRED EMBODIMENT

Figure 1:
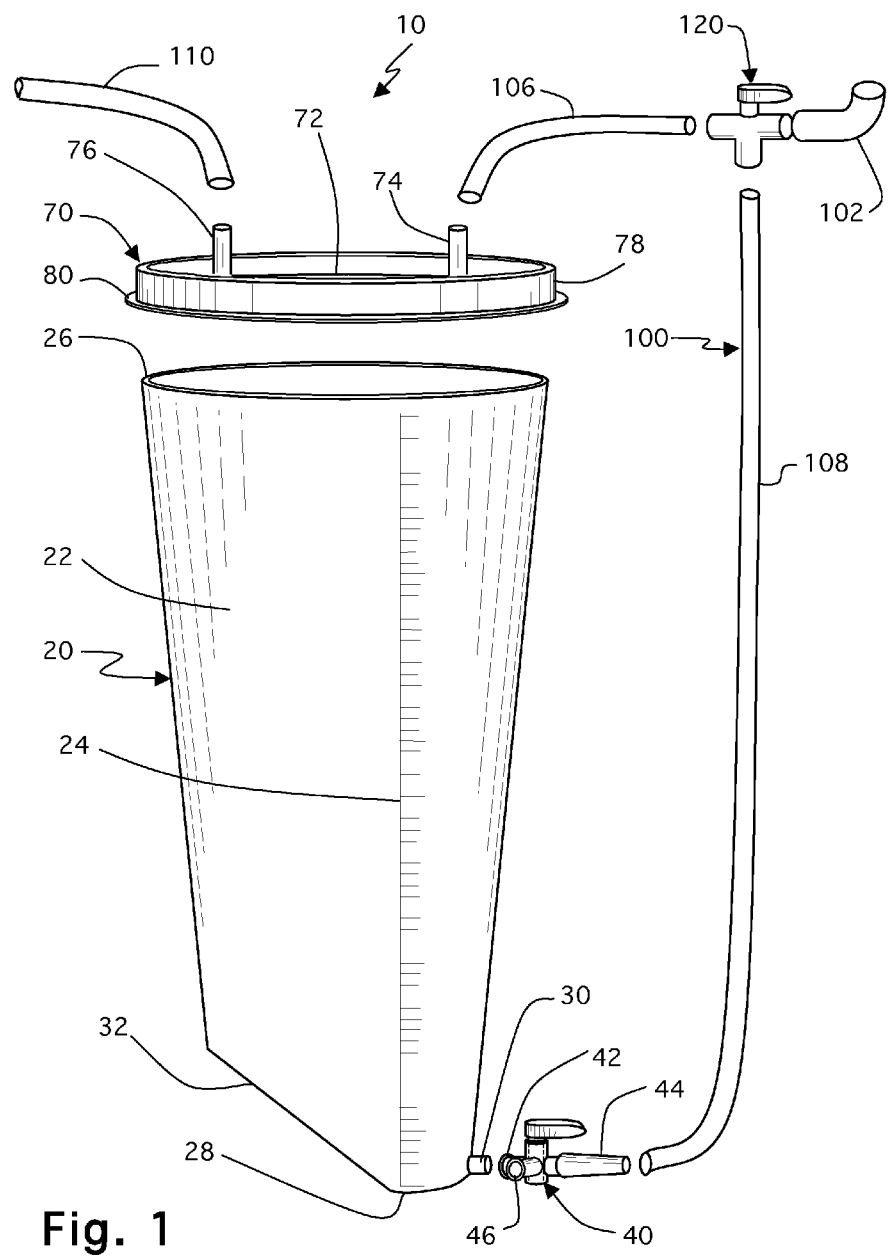
FIG. 1 represents an exploded view of a fat harvesting container, object of the instant invention.

Referring now to the drawings, the present invention is generally referred to with numeral 10. It can be observed that it basically includes container assembly 20, lid assembly 70, and tubing assembly 100.

As seen in FIG. 1, container assembly 20 is preferably rigid and is made of a transparent material. In the preferred embodiment, container assembly 20 has a substantially cylindrical tapered shape. Container assembly 20 comprises exterior wall 22 with measurement indicator 24. A first section of exterior wall 22 extends from top edge 26 to base 28, and a second section of exterior wall 22 extends from top edge 26 to inclined wall 32. Inclined wall 32 extends from the second section of exterior wall 22 to base 28. Outlet 30 has a substantially tubular shape and is adjacent to base 28. Although not illustrated, container assembly 20 may rest within a solid or semi-solid base to remain in an upright position as illustrated in the figures.

In the preferred embodiment, valve assembly 40 is a three-way valve and comprises suction inlet 42, suction outlet 44, and syringe outlet 46. Valve assembly 40 is removably mounted onto outlet 30 with suction inlet 42.

Lid assembly 70 is preferably made of a semi-flexible material. Lid assembly 70 comprises top wall 72 having outlet post 74 and inlet post 76, and sidewall 78. Although not required, lid assembly 70 may also comprise lip 80. Although not seen, lid assembly 70 also comprises a circular channel that aligns with to receive top edge 26 when lid assembly 70 is placed upon top edge 26 with a predetermined force to hermetically seal container assembly 20. In an alternate embodiment, lid assembly 70 may be permanently affixed onto or be a single embodiment with container assembly 20.

Tubing assembly 100 comprises suction tube 102, outlet tube 106, bypass tube 108, inlet tube 110, and valve assembly 120. Suction tube 102 is connected to a vacuum pump liposuction machine, not shown, at a suction tube 102 first end, and to valve assembly 120 at a suction tube 102 second end. Valve assembly 120 also receives an outlet tube 106 first end, and a bypass tube 108 first end. An outlet tube 106 second end connects to outlet post 74, and a bypass tube 108 second end is connected to suction outlet 44. An inlet tube 110 first end connects to tooling to obtain matter from a patient. Such tooling can be a syringe, not shown. An inlet tube 110 second end connects to inlet post 76. Although not illustrated, it is noted that tubing assembly 100, including suction tube 102, outlet tube 106, bypass tube 108, inlet tube 110, and valve assemblies 40 and 120 may comprise luer locks or similar locking and/or fastening systems.

Figure 2:
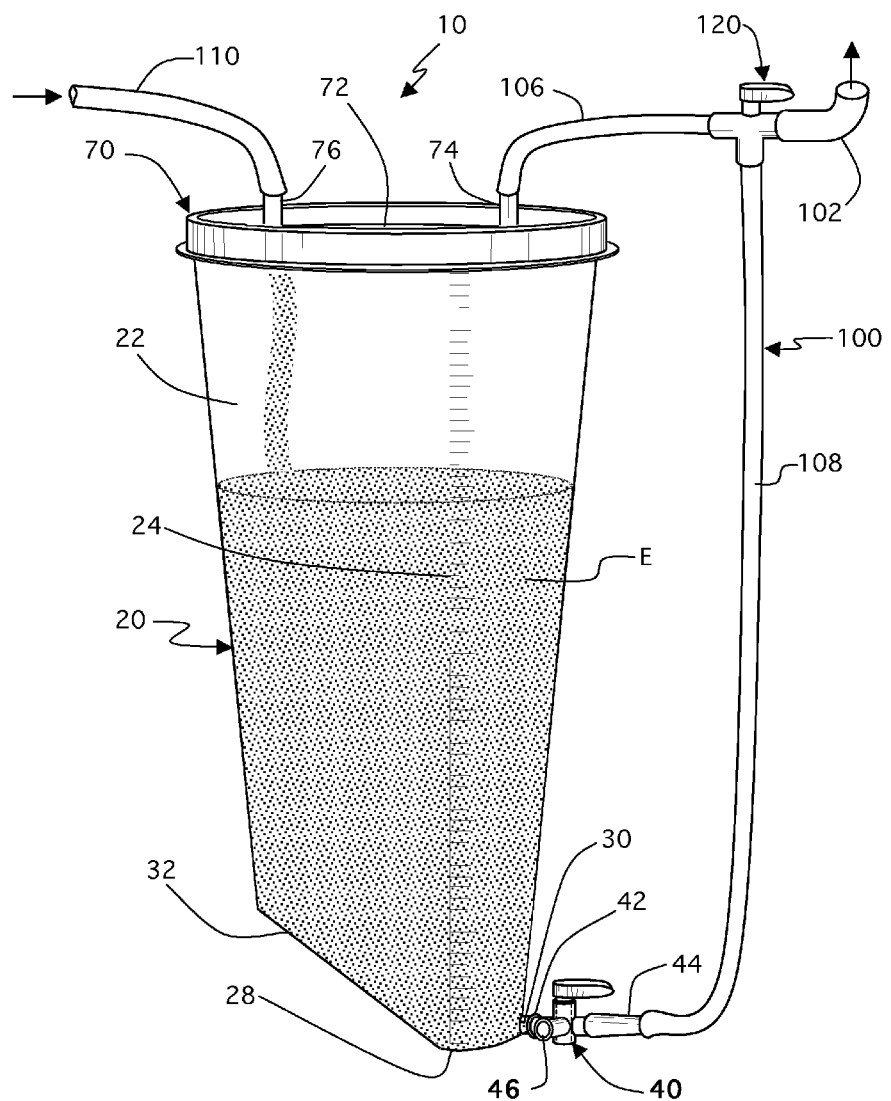
FIG. 2 is an isometric view of the instant invention during a liposuction procedure, showing an emulsion of liquid matter and fat matter being suctioned from a human body through an inlet tube and into a container assembly.
Figure 3:
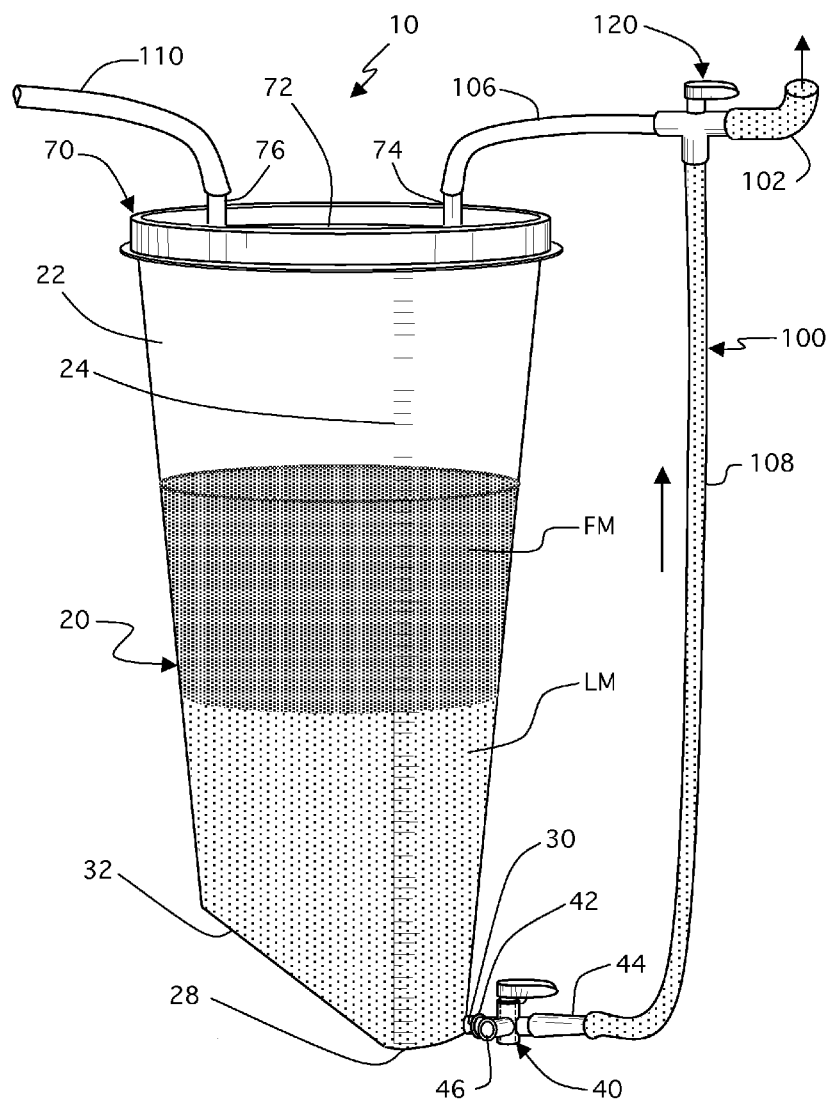
FIG. 3 is an isometric view of the instant invention after the liposuction procedure, showing a natural separation of liquid matter from fat matter that occurs within the container assembly and the liquid matter being removed from within the container assembly.

As seen in FIG. 2, during a liposuction procedure, matter; defined as emulsion E, containing liquid matter LM and fat matter FM, seen in FIG. 3, is vacuumed from a patient through inlet tube 110 and into container assembly 20. Vacuum pressure is created within container assembly 20, inlet tube 110, and the syringe by the vacuum pump liposuction machine connected to suction tube 102. It is noted that in some cases, the matter, defined as emulsion E, may also comprise blood and blood tissue, and other emulsion fluids. Emulsion E may also comprise chemical compositions or solutions such as saline that are typically used by the plastic, dermatological, and cosmetic surgeons, also defined as practitioners, to improve the process of fat harvesting, whereby saline is first introduced or injected into the patient before the liposuction procedure. Although not illustrated, it is noted that in the event of large displacements of emulsion E during a liposuction procedure, emulsion E may be discarded through bypass tube 108. Such an event occurs if the capacity of container assembly 20 is not sufficient for emulsion E. In that case, valve assembly 40 is operated to open suction outlet 44 to allow emulsion E to be discarded through bypass tube 108. If necessary, valve assembly 120 may be operated to close outlet tube 106, thus creating greater vacuum pressure within bypass tube 108. Alternatively, valve assembly 120 may be operated to also open outlet tube 106, thus adjusting vacuum pressure within bypass tube 108.

As seen in FIG. 3, after the liposuction procedure is complete, a natural separation of liquid matter LM from fat matter FM occurs within container assembly 20 after a first predetermined time period. The natural separation occurs because fat matter FM is lighter than liquid matter LM, blood and blood tissue, and chemical compositions or solutions such as saline. After the first predetermined time period, valve assembly 40 is operated to open suction outlet 44 to allow liquid matter LM, blood and blood tissue, and chemical compositions or solutions such as saline to be discarded through bypass tube 108, whereby vacuum pressure is created within bypass tube 108 by the vacuum pump liposuction machine. If necessary, valve assembly 120 may be operated to close outlet tube 106, thus creating greater vacuum pressure within bypass tube 108. Inclined wall 32 biases liquid matter LM towards outlet 30, thus facilitating its exit therethrough with minimum movement of liquid matter LM and fat matter FM within container assembly 20. Thus, having funnel-type effect. This way liquid matter LM and fat matter FM remain separate and a probability of remixing is reduced and prevented.

Figure 4:
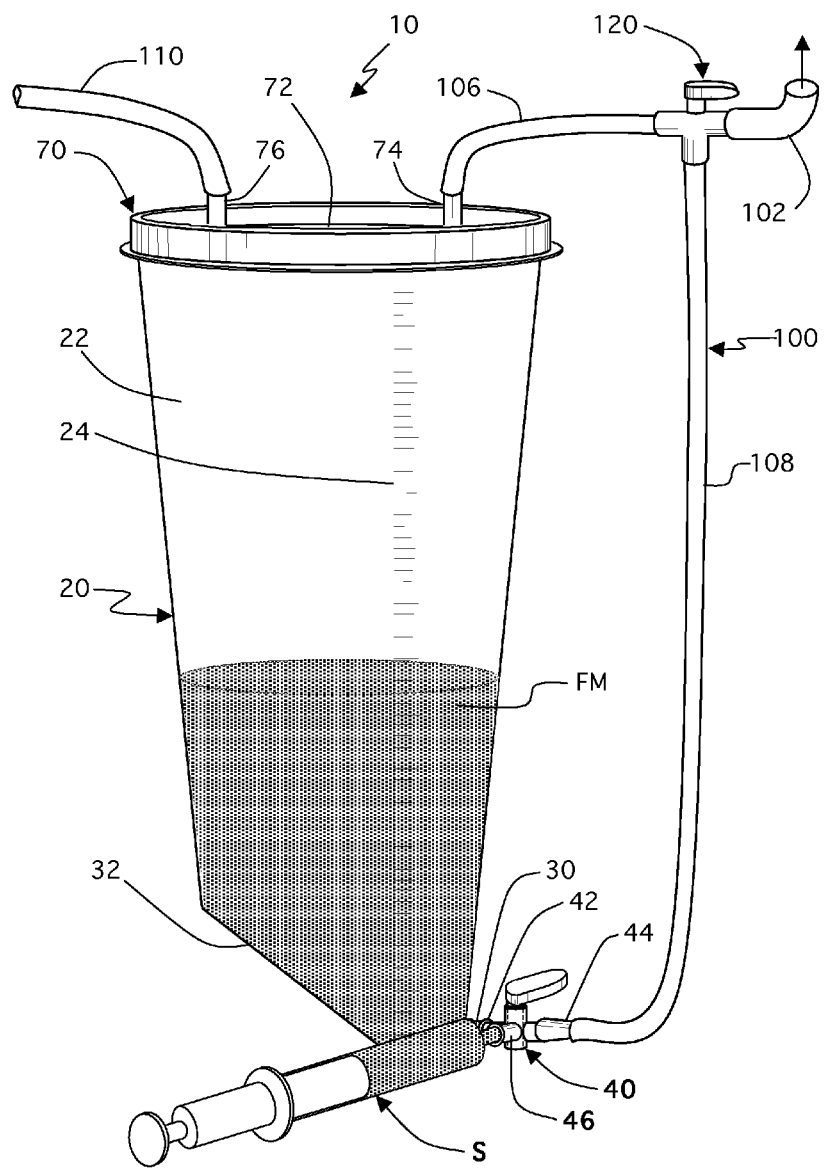
FIG. 4 is an isometric view of the instant invention after the liposuction procedure, showing the fat matter being transferred into a syringe after the liquid matter has been removed from within the container assembly.

As seen in FIG. 4, after liquid matter LM, blood and blood tissue, emulsion fluids, and chemical compositions or solutions such as saline are discarded through bypass tube 108, the practitioner operates valve assembly 40 to open syringe outlet 46 so that syringe S, as a transplantation syringe, can be used to withdraw a desired amount of fat matter FM therefrom, to then introduce or inject it into the desired location of the patient.

Instant invention 10 therefore safely harvests the human body fat defined as fat matter FM, whereby it minimizes exposure to air and bacteria to reduce contamination risks. Instant invention 10 improves the viability of fat matter FM, whereby it minimizes manipulation of emulsion E contained therein. Furthermore, instant invention 10 maximizes sterility of emulsion E and specifically fat matter FM, during a fat collection and preparation process, so that the fat matter FM can be introduced or injected into the desired location of the patient.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A fat harvesting container, comprising:
   A) a transparent container assembly having a top edge, a base, an exterior wall with first and second sections, and an inclined wall, said first section extends from said top edge to said base, said second section extends from said top edge to said inclined wall, and said inclined wall extends from said second section to said base, said transparent container assembly also comprises a first outlet, said transparent container assembly further comprises a first valve assembly, said first valve assembly comprises a second inlet, a third outlet, and a fourth outlet, said first valve assembly is removably mounted onto said first outlet;
   B) a lid assembly; and
   C) a tubing assembly.

2. The fat harvesting container set forth in claim 1, further characterized in that said first outlet is adjacent to said base.

3. The fat harvesting container set forth in claim 1, further characterized in that said exterior wall comprises a measurement indicator.

4. The fat harvesting container set forth in claim 1, further characterized in that said lid assembly comprises a top wall having a second outlet and a first inlet, said lid assembly also comprises a sidewall and a channel that aligns with to receive said top edge when said lid assembly is placed thereon with a predetermined force to seal said transparent container assembly.

5. The fat harvesting container set forth in claim 4, further characterized in that said tubing assembly comprises at least first, second, third, and fourth tubes, and a second valve assembly.

6. The fat harvesting container set forth in claim 5, further characterized in that said first tube is connected to a vacuum pump and to said second valve.

7. The fat harvesting container set forth in claim 6, further characterized in that said second tube is connected to said second valve assembly and said second outlet.

8. The fat harvesting container set forth in claim 7, further characterized in that said third tube is connected to said first inlet and tooling to obtain emulsion from a patient.

9. The fat harvesting container set forth in claim 8, further characterized in that said fourth tube is connected from said third output of said first valve assembly to said second valve assembly.

10. A fat harvesting container, comprising:
    A) a transparent container assembly having a top edge, a base, an exterior wall with first and second sections, and an inclined wall, said first section extends from said top edge to said base, said second section extends from said top edge to said inclined wall, and said inclined wall extends from said second section to said base, said transparent container assembly also comprises a first outlet;
    B) a lid assembly comprising a top wall having a second outlet and a first inlet, said lid assembly also comprises a sidewall and a channel that aligns with to receive said top edge when said lid assembly is placed thereon with a predetermined force to seal said transparent container assembly;
    C) a tubing assembly; and
    D) a first valve assembly comprising a second inlet, a third outlet, and a fourth outlet, said first valve assembly is removably mounted onto said first outlet.

11. The fat harvesting container set forth in claim 10, further characterized in that said tubing assembly comprises at least first, second, third, and fourth tubes, and a second valve assembly.

12. The fat harvesting container set forth in claim 11, further characterized in that said first tube is connected to a vacuum pump and to said second valve.

13. The fat harvesting container set forth in claim 12, further characterized in that said second tube is connected to said second valve assembly and said second outlet.

14. The fat harvesting container set forth in claim 13, further characterized in that said third tube is connected to said first inlet and tooling to obtain emulsion from a patient.

15. The fat harvesting container set forth in claim 14, further characterized in that said fourth tube is connected from said third output of said first valve assembly to said second valve assembly.

* * * * *